(12) United States Patent
Simon-Lopez

(10) Patent No.: US 8,154,713 B2
(45) Date of Patent: Apr. 10, 2012

(54) METHODS OF DETERMINATION OF IRON DEFICIENCY AND HEMOCHROMATOSIS

(75) Inventor: Ramon Simon-Lopez, St. Cergue (CH)

(73) Assignee: Beckman Coulter, Inc., Brea, CA (US)

( * ) Notice: Subject to any disclaimer, the term of this patent is extended or adjusted under 35 U.S.C. 154(b) by 464 days.

(21) Appl. No.: 12/550,626

(22) Filed: Aug. 31, 2009

(65) Prior Publication Data

US 2010/0003713 A1 Jan. 7, 2010

Related U.S. Application Data

(62) Division of application No. 11/524,682, filed on Sep. 21, 2006, now Pat. No. 7,609,369.

(60) Provisional application No. 60/719,849, filed on Sep. 24, 2005.

(51) Int. Cl.
*G01N 33/48* (2006.01)
(52) U.S. Cl. ............................................ 356/39; 702/21
(58) Field of Classification Search ........................ None
See application file for complete search history.

(56) References Cited

U.S. PATENT DOCUMENTS 5,281,519 A * 1/1994 Schechter et al. ........... 435/6.11
2003/0232393 A1* 12/2003 Roddiger et al. .............. 435/7.1

* cited by examiner

*Primary Examiner* — Rebecca Prouty
*Assistant Examiner* — Paul Martin
(74) *Attorney, Agent, or Firm* — K&L Gates LLP; Louis C. Cullman; Dean G. Stathakis

(57) ABSTRACT

New diagnostic parameters or indexes for detection of absolute iron deficiency, latent iron deficiency, functional iron deficiency, or latent functional iron deficiency have been disclosed. The parameters include a RBC size factor, $RSf_1$ defined by the formula of $(MCV \times MRV)^{1/2}$, or $RSf_2$ defined by the formula of $(MCV \times MRV)/100$, a volume-hemoglobin factor (VHf) defined by the formula of $(MCV \times Hgb)/100$, and a volume-hemoglobin/distribution factor (VHDWf) defined by the formula of $(MCV \times Hgb)/(RDW \times 10)$. Further disclosed are the methods of using these parameters for detection of absolute iron deficiency, latent iron deficiency, functional iron deficiency, or latent functional iron deficiency. Also disclosed is a method of using RSf for detection of hemochromatosis.

10 Claims, 3 Drawing Sheets

METHODS OF DETERMINATION OF IRON DEFICIENCY AND HEMOCHROMATOSIS

CROSS REFERENCE TO RELATED APPLICATION

This application is a divisional of patent application Ser. No. 11/524,682, filed Sep. 21, 2006 now U.S. Pat. No. 7,609,369, which claims the benefit under 35 USC 119(e) of the provisional patent application Ser. No. 60/719,849, filed Sep. 24, 2005. Both parent applications are hereby incorporated by reference in their entirety.

FIELD OF THE INVENTION

The present invention relates to methods of detection of iron deficiency and hemochromatosis using specific functions of red blood cell and reticulocyte parameters.

BACKGROUND OF THE INVENTION

Iron deficiency (ID) is the most prevalent single deficiency state on a worldwide basis. It is important economically because it diminishes the capability of individuals who are affected to perform physical labor, and it diminishes both growth and learning in children.

Absolute iron deficiency, with anemia or without anemia, and functional iron deficiency (FID) are high frequency clinical conditions, and these patients have iron deficient erythropoiesis. Absolute iron deficiency is defined as a decreased total iron body content. Iron deficiency anemia (IDA) occurs when iron deficiency is sufficiently severe to diminish erythropoiesis and cause the development of anemia. Functional iron deficiency describes a state where the total iron content of the body is normal or even elevated, but the iron is 'locked away' and unavailable for the production of red blood cells. This condition is observed mainly in patients with chronic renal failure who are on hemodialysis.

Iron status can be measured using hematological and biochemical indices. Each parameter of iron status reflects changes in different body iron compartments and is affected at different levels of iron depletion. Specific iron measurements include hemoglobin (Hgb), mean cell volume (MCV), hematocrit (Hct), erythrocyte protoporphyrin, plasma iron, transferrin, transferrin saturation levels (TSAT), serum ferritin (SF) and more recently soluble transferrin receptors (sTfR) and red-cell distribution width (RDW).

Typical values for normal iron status are SF 100±60 ng/ml and Hgb 12-17 g/dl for women and 14-19 g/dl for men. The typical values for latent iron deficiency are SF <22 ng/ml and Hgb normal to slightly low. The typical values for iron deficiency anemia are SF <22 ng/ml, Hgb for women <12 g/dl and for men <13 g/dl.

Hemoglobin (Hgb) has been used longer than any other iron status parameter. It provides a quantitative measure of the severity of iron deficiency once anemia has developed. Hemoglobin determination is a convenient and simple screening method and is especially useful when the prevalence of iron deficiency is high, as in pregnancy or infancy. The limitations of using hemoglobin as a measure of iron status are its lack of specificity (as factors such as $B_{12}$ or folate deficiency, genetic disorders and chronic infections can limit erythropoiesis) and its relative insensitivity due to the marked overlap in values between normal and iron deficient populations. To identify iron deficiency anemia, hemoglobin is measured together with more selective measurements of iron status.

A reduction in mean cell volume (MCV) occurs when iron deficiency becomes severe, at about the same time as anemia starts to develop. It is a fairly specific indicator of iron deficiency once thalassemia and the anemia of chronic disease have been excluded. A cut-off value of 80 fl is accepted as the lower limit of normal in adults.

The red-cell distribution width (RDW) has been used recently in combination with other parameters for the classification of anemias. It reflects the variation in the size of the red cells and can be used to detect subtle degrees of anisocytosis. RDW is computed directly form the RBC histogram. Two different calculated values have been provided on hematology analyzers. The RDW-CV is measured as a ratio of the width of the distribution curve at one standard deviation divided by the MCV. The RDW-SD is a direct measurement of the distribution width at the 20% frequency level. Normally, the size distribution curve for red blood cells is quite symmetrical, with an RDW-CV value of 10±1.5% and an RDW-SD of 42±5 (fl). A high RDW, which means a greater variation in cell size, is caused by either the appearance of macrocytic or microcytic cells. An elevated red-cell distribution width appears to be the earliest hematological manifestation of iron deficiency.

The most commonly used iron status parameters at present are transferrin saturation (TSAT) and serum ferritin (SF). However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity (TIBC), a measurement of circulating transferrin, and multiplying by 100. Ferritin is a storage protein that is contained primarily within the reticuloendothelial system (RES), with some amounts released in the serum. Under conditions of iron excess, ferritin production increases to offset the increase in plasma iron. The level of ferritin in the serum, therefore, reflects the amount of iron in storage.

For patients with chronic kidney disease, absolute iron deficiency may be diagnosed when TSAT is <20% and SF is <100 ng/ml. Functional iron deficiency may be more difficult to diagnose since iron status parameters may indicate adequate iron stores. There are different criteria in defining FID, one of them is published by the Kidney Disease Outcomes Quality Initiative—K/DOQI (Eknoyan G, et al. Continuous quality improvement: DOQI becomes K/DOQI and is updated. National Kidney Foundation's Dialysis Outcomes Quality Initiative. *Am J Kidney Dis.*, 2001 January; 37(1): 179-194), as shown in the following table.

| Definition of Functional Iron Deficiency (FID) and Absolute Iron Deficiency (AID) by Kidney Disease Outcomes, Quality Initiative K/DOQI (U.S.A) | | |
|---|---|---|
| Ferritin μg/L | <100 | 100-800 |
| TSAT <20% | AID | |
| TSAT 20%-50% | | FID |

The limitations of using transferrin saturation reflect those of serum iron, i.e., wide diurnal variation and low specificity. TSAT is also reduced in inflammatory disease. Transferrin saturation is commonly used in population studies combined with other indicators of iron status. On the other hand, as ferritin is an acute phase reactant, its serum levels may be elevated in the presence of chronic inflammation, infection, malignancy and liver disease. Alcohol consumption has also been suggested to independently raise serum ferritin.

Recently, several new red blood cell and reticulocyte parameters have been reported having utilities in detection of iron deficiency and functional iron deficiency. Two of the parameters are hypochromic red cells % (referred to as % Hypo) and CHr (reticulocyte hemoglobin content) reported by the Bayer ADVIA® 120 hematology analyzer (Thomas C. et al. Biochemical Markers and Hematologic Indices in the Diagnosis of Functional Iron Deficiency. *Clinical Chemistry* 48:7, 1066-1076, 2002). CHr is defined by the formula (CHr=MCVr×CHCMr), wherein MCVr is the mean reticulocyte cell volume and CHCMr is the mean hemoglobin concentration of reticulocytes which is obtained by an optical cell-by-cell hemoglobin measurement.

Reticulocytes are immature red blood cells with a life span of only 1 to 2 days. When these are first released from the bone marrow, measurement of their hemoglobin content can provide the amount of iron immediately available for erythropoiesis. A less than normal hemoglobin content in these reticulocytes is an indication of inadequate iron supply relative to demand. The amount of hemoglobin in these reticulocytes also corresponds to the amount of hemoglobin in mature red blood cells. CHr has been evaluated recently in numerous studies as a test for iron deficiency and functional iron deficiency and has been found to be highly sensitive and specific. However, exact threshold values have not been established, as the threshold values vary depending on the laboratory and instrument used.

Epoetin is effective in stimulating production of red blood cells, but without an adequate iron supply to bind to heme, the red blood cells will be hypochromic, i.e., low in hemoglobin content. Thus, in states of iron deficiency, a significant percentage of red blood cells leaving the bone marrow will have a low hemoglobin content. By measuring the percentage of red blood cells with hemoglobin content <28 g/dl, iron deficiency can be detected. Hypochromic red cells percentages >10% have been correlated with iron deficiency. % Hypo is reported by Bayer ADVIA 120 hematology analyzer based on the optical cell-by-cell hemoglobin measurement.

Two other parameters have been reported recently correlating to % Hypo and CHr are RBC-Y and RET-Y reported by the SYSMEX® XE-2100 hematology analyzer (Machin S. J. et al. Functional Iron Deficiency and New Red Cell Parameters on the Sysmex XE-2100, ISLH 2001 Industry-Sponsored Workshops, ISLH XIVth International Symposium. 2001). RBC-Y is the mean value of the forward light scatter histogram within the mature erythrocyte population, and RET-Y is the mean value of the forward light scatter histogram within the reticulocyte population obtained in a reticulocyte measurement on the SYSMEX® XE-2100 hematology analyzer.

Another parameter that has been used previously for detection of iron deficiency is the ratio of MRV/MCV, or ln (MRV/MCV) (referred to as dR), wherein MRV is the mean reticulocyte cell volume and MCV is the mean red blood cell volume. Typically, the ratio of MRV/MCV >1.35 is considered as the indication of iron deficiency.

Furthermore, in a different aspect from assisting diagnosis and treatment of diseases, it is desirable to detect certain hematological conditions before the occurrence of the diseases. It is well known that latent iron deficiency (LID) has a high frequency in fertile women, due to menstruation and sometimes due to poor diet. Latent iron deficiency refers to the presence of iron deficiency but not yet anemia. Also well known is the relatively high frequency of latent functional iron deficiency (LFID) and hemochromatosis (HEM) in the general population. Latent functional iron deficiency refers to the pre-anemic stage of functional Iron deficiency. On the other hand, hemochromatosis, the most common form of iron overload disease, is an inherited disorder that causes the body to absorb and store too much iron. The extra iron builds up in organs and causes damages to the organs. Without treatment, the disease can cause these organs to fail. Clinically, it is important to detect these conditions early in order to provide preventative treatments.

It is desirable to be able to detect iron deficiency, such as absolute iron deficiency, latent iron deficiency, functional iron deficiency and latent functional iron deficiency, using existing hematology parameters reported on an automated hematology analyzer during a blood analysis routinely performed on the instrument, which can assist in early detection of the clinical conditions, without additional cost.

SUMMARY OF THE INVENTION

In one aspect, the present invention provides methods of detection of absolute iron deficiency, latent iron deficiency, functional iron deficiency, or latent functional iron deficiency using functions of red blood cells and reticulocytes.

In one embodiment, the method comprises analyzing a blood sample of the patient on a hematology analyzer and obtaining the mean cell volume of red blood cells (MCV) and the mean cell volume of reticulocytes (MRV) of the blood sample; obtaining a RBC size factor (RSf) defined as a product function of the MCV and the MRV; comparing the RSf to a predetermined criterion; and reporting an indication of iron deficiency if the RSf meets the predetermined criterion. Herein, RSf is either $RSf_1$ defined by the formula of $(MCV \times MRV)^{1/2}$, or $RSf_2$ defined by the formula of $(MCV \times MRV)/100$.

In another embodiment, the method comprises analyzing a blood sample of the patient on a hematology analyzer and obtaining MCV and a total hemoglobin concentration (Hgb) of the blood sample; obtaining a volume-hemoglobin factor (VHf) defined as a product function of MCV and Hgb; comparing the VHf to a predetermined criterion; and reporting an indication of iron deficiency if the VHf meets the predetermined criterion. Herein, VHf is defined by the formula of $(MCV \times Hgb)/100$.

In a further embodiment, the method comprises analyzing a blood sample of the patient on a hematology analyzer and obtaining MCV, Hgb, and the red blood cell distribution width (RDW) of the blood sample; obtaining a volume-hemoglobin/distribution factor (VHDWf) defined as a function of MCV, Hgb and RDW; comparing the VHDWf to a predetermined criterion; and reporting an indication of iron deficiency if the VHDWf factor meets the predetermined criterion. Herein, VHDWf is defined by the formula of $(MCV \times Hgb)/(RDW \times 10)$.

In another aspect, the present invention provides a method of detection of hemochromatosis using RSf. The method comprises analyzing a blood sample of the patient on a hematology analyzer and obtaining RSf from the MCV and the MRV of the blood sample; comparing the RSf to a predetermined criterion; and reporting an indication of hemochromatosis if the RSf meets the predetermined criterion.

In a further aspect, the present invention provides methods of producing the above defined functions or indexes on hematology analyzers.

In one embodiment, a method of producing a RBC size factor (RSf) of a blood sample on a hematology analyzer comprises mixing a first aliquot of a blood sample with a blood diluent to form a first sample mixture, analyzing the first sample mixture on the hematology analyzer, and obtaining a mean corpuscular volume of red blood cells (MCV); exposing a second aliquot of the blood sample with a reticulocyte reagent system to form a second sample mixture, analyzing the second sample mixture on the hematology analyzer, and obtaining a mean corpuscular volume of reticulocytes (MRV); obtaining the RBC size factor (RSf$_1$ or RSf$_2$) using the obtained MCV and MRV; and reporting the RSf of the blood sample on the hematology analyzer.

In another embodiment, a method of producing a volume-hemoglobin factor (VHf) of a blood sample on a hematology analyzer comprises mixing a first aliquot of a blood sample with a blood diluent to form a first sample mixture, analyzing the first sample mixture on the hematology analyzer, and obtaining a mean corpuscular volume of red blood cells (MCV); reacting a second aliquot of the blood sample with a reagent system to form a second sample mixture, analyzing the second sample mixture on the hematology analyzer, and obtaining a total hemoglobin concentration (Hgb); obtaining the volume-hemoglobin factor (VHf) using the obtained MCV and Hgb; and reporting the VHf of the blood sample on the hematology analyzer.

This method can further comprise producing a volume-hemoglobin/distribution factor (VHDWf), wherein the method further comprises obtaining a distribution width of the red blood cells (RDW) from the analysis of the first sample mixture; obtaining the VHDWf using the obtained MCV, Hgb, and RDW, and reporting the VHDWf of the blood sample on the hematology analyzer.

The advantages of the present invention will become apparent from the following description taken in conjunction with the accompanying drawings showing exemplary embodiments of the invention.

DETAILED DESCRIPTION OF THE INVENTION

Figure 1:
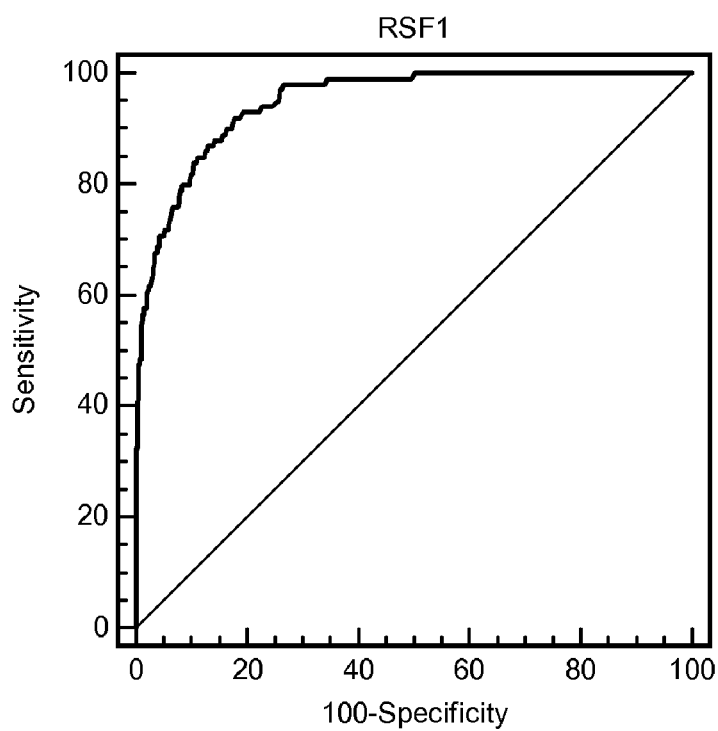
FIG. 1 is the ROC curve of RSf$_1$, using CHr as the criterion for detection of absolute iron deficiency and functional iron deficiency, as described in Example 1.

In one aspect, the present invention provides a method for detection of iron deficiency using specific functions of red blood cell and reticulocyte parameters. The term of iron deficiency used herein includes absolute iron deficiency (ID), latent iron deficiency (LID), functional iron deficiency (FID) and latent functional iron deficiency (LFID).

Absolute iron deficiency, frequently referred to as iron deficiency in the literature, is defined as a decreased total iron body content. Iron deficiency anemia (IDA) occurs when iron deficiency is sufficiently severe to diminish erythropoiesis and cause the development of anemia. Latent iron deficiency refers to the presence of iron deficiency but not yet anemia. On the other hand, functional iron deficiency defines a state where the total iron content of the body is normal or even elevated, but the iron is unavailable for the production of red blood cells. This condition is observed mainly in patients with chronic renal failure who are on hemodialysis. Latent functional iron deficiency refers to the pre-anemic stage of functional Iron deficiency. Individuals having different forms of iron deficiency, as described above, have different extents of iron deficient erythropoiesis.

In one embodiment, the method uses a product function of the mean cell volume of red blood cells (MCV) and the mean cell volume of reticulocytes (MRV) of a blood sample, which is herein referred to as RBC size factor (RSf), for detection of iron deficiency, including absolute iron deficiency and functional iron deficiency. More specifically, the method comprises the following steps: (a) analyzing a blood sample of a patient on a hematology analyzer and obtaining MCV and MRV of the blood sample; (b) obtaining RSf of the blood sample; (c) comparing the RSf to a predetermined criterion; and (d) reporting an indication of iron deficiency if the RSf meets the predetermined criterion.

In one preferred embodiment, RSf is defined by the formula of $(MCV \times MRV)^{1/2}$, which is herein referred to as RSf$_1$. In an alternative embodiment, RSf is defined by the formula of $(MCV \times MRV)/100$, which is herein referred to as RSf$_2$. The predetermined criterion is typically a cut-off value of a specific diagnostic parameter, as described in detail hereinafter in various embodiments of the present invention. One frequently used criterion is the cut-off value of the receiver operating characteristic (ROC) analysis of a specific parameter or index.

For measuring the red blood cells a blood sample is typically diluted substantially with a diluent in a sample chamber or bath. Using an impedance measurement with a non-focused flow aperture, the blood sample can be diluted with a dilution ratio of about 6250:1. When a focused flow flowcell is used for the measurement, the dilution ratio can be substantially lower, such as 290:1. To maintain red blood cell volume and morphology during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526.

When a particle or a blood cell, suspended in a conductive solution, passes through a flow cell or an aperture, an electrical signal, or a pulse, can be measured due to the increase of impedance. The electrical pulses have been used for counting the number of blood cells of a blood sample. On the other hand, the pulse shape, height and width are directly related to the volume or size of a particle, and can be converted to the volume of the cell measured. When a sample that contains two or more different blood cells having different volumes is measured, a histogram obtained from the measurement can represent volume distribution of these blood cells. The detection methods and apparatus used for blood cell counting and sizing by a blood analyzer equipped with a DC impedance measurement device are generally described in U.S. Pat. Nos. 2,656,508, 3,810,011 and 5,125,737, which are hereby incorporated by reference in their entirety. Herein, the phrase "blood cell sizing" refers to the cell volume measurement.

Alternatively, low angle light scatter measurement can also be used for counting and sizing the blood cells. Herein, the term "low angle light scatter" refers to light scatter signals measured in a range in less than 100 from the incident light.

In the cell volume measurement, a cell volume distribution histogram is obtained. For the red blood cell measurement, the obtained histogram is referred to as the red blood cell distribution histogram. For a normal blood sample, a narrow and well defined red blood cell distribution, typically a Gaussian distribution, is obtained. For clinically abnormal blood samples, various distortions of the distribution have been observed, such as shift of the distribution to either higher or lower volume side, asymmetric distribution, population extension on either the higher or lower volume side, or both sides. The mean cell volume (MCV) and red blood cell distribution width (RDW) are calculated from the red blood cell distribution histogram.

The total hemoglobin concentration (Hgb) of a blood sample is typically measured on an automated hematology analyzer by mixing an aliquot of the blood sample with a lytic reagent. Upon exposing to the lytic reagent, the red blood cells are completely lysed, and hemoglobins are released to the sample mixture, which upon contacting with a ligand in the lytic reagent forms a chromogen. The hemoglobin chromogen is then measured by UV-VIS spectroscopy at a predetermined wavelength, and Hgb is calculated from the measurement.

One lysing reagent system suitable for measuring Hgb comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102, these are hereby incorporated by reference in their entirety. Alternatively, the reagent system can also be a single lysing reagent as described in U.S. Pat. No. 5,882,934 which is hereby incorporated by reference in its entirety. Furthermore, various lytic reagents known in the art for measurement of hemoglobin can be used for the purpose of the present invention.

Reticulocytes in a blood sample are measured and reported on several high end hematology analyzers in routine sample analysis, using light scatter, absorption, impedance and/or combination thereof. Most commonly reported parameters include reticulocyte percent (RET %) and absolute number (RET #), mean reticulocyte volume (MRV), and immature reticulocyte fraction (IRF). Depending on the specific measurement method, other reticulocyte parameters are also provided by the hematology analyzers.

On the Coulter LH750 or Coulter GEN*S™ hematology analyzer (Beckman Coulter, Inc. Fullerton, Calif.), several aliquots of a blood sample are analyzed concurrently in different analysis modes. In the CBC mode, a first aliquot of a blood sample is diluted by an isotonic blood diluent to form a first sample mixture, and red blood cells and platelets are measured from the first sample mixture. At the same time, a second aliquot of the blood sample is mixed with a blood diluent and a lytic reagent to form a second sample mixture from the second sample mixture, and hemoglobin and white blood cells are measured. Various red blood cell parameters, among others, are reported from the measurements, which include mean cell volume (MCV), red blood cell distribution width (RDW), total hemoglobin concentration (Hgb), and derivative parameters, such as mean corpuscular hemoglobin (MCH), mean corpuscular hemoglobin concentration (MCHC), and etc. The RDW reported on these hematology analyzers is RDW-CV, which is measured as a ratio of the width of the distribution curve at one standard deviation divided by the MCV.

In the Retic mode, a third aliquot of the blood sample is exposed to a reticulocyte reagent system. More specifically, the third aliquot of the blood sample is mixed with a reticulocyte stain reagent which contains methylene blue, and then mixed with a lysing/fixing reagent to form the third sample mixture. Methylene blue, a non-fluorochrome dye, is used to precipitate the residual RNA within the reticulocytes, thereby achieving differentiation of the reticulocytes from mature red blood cells. The third sample mixture is then measured by the VCS detection method. Among other reticulocyte parameters, MRV, mean spherized cell volume (MSCV), immature reticulocyte fraction (IRF), and high light scatter reticulocyte percent and absolute number (HLR % and #) are reported by the instrument. The reticulocytes can also be measured using fluorescence measurements, as known on various commercial hematology analyzers.

Herein, the VCS detection method or technology refers to a multidimensional measurement of direct current (DC) and radio frequency (RF) and medium angle light scatter (LS) signals generated by a cell passing through a focused flow cell. Among these three measurements, both DC and RF measurements are impedance measurements, which detect the increase of impedance as a cell carried in a conductive medium passes through the flow cell. This technology has been fully described in U.S. Pat. No. 5,125,737, which is herein incorporated by reference in its entirety.

As discussed above, CHr (reticulocyte hemoglobin content) reported by the Bayer hematology analyzer has been used for detection of iron deficiency and functional iron deficiency in the recent years and has been found to be highly sensitive and specific. Typically, a cut-off value of CHr <28 pg or <29 pg is used for determining absolute iron deficiency and functional iron deficiency. On the other hand, hypochromic red cells percentages have also been used for determining iron deficiency. % Hypo <5% is considered normal. Two different criteria, more specifically, % Hypo >5% and >10% have been used. % Hypo >10% has been more commonly used for defining absolute iron deficiency and functional iron deficiency (Locatelli, F et al., Revised European best practice guidelines for the management of anaemia in patients with chronic renal failure, *Nephrology and Dialysis Transplantation*, Volume 19 May 2004 (Supplement 2)).

Example 1 illustrates the method of the present invention using $RSf_1$ for detection of iron deficiency in comparison to CHr. As shown, 981 clinical whole blood samples were analyzed on Coulter LH750 and GEN*S hematology analyzers, and $RSf_1$ was calculated for each blood sample using MCV and MRV reported on the hematology analyzers. The same blood samples were also analyzed on Bayer ADVIA 120 hematology analyzer. A receiver operating characteristic (ROC) analysis of $RSf_1$ was performed using CHr <28 pg as the criterion for defining abnormal, i.e., absolute iron deficiency and functional iron deficiency. Using this criterion, 99 samples were considered abnormal and 882 considered normal.

FIG. 1 shows the obtained ROC curve of $RSf_1$. On the y-axis is plotted sensitivity (true positive fraction) and on the x-axis is plotted 100-specificity (false positive fraction). A test with perfect discrimination has an ROC curve that passes through the upper left corner, where the true-positive fraction is 100% (perfect sensitivity). The theoretical curve for a test with no discrimination is 450 diagonal line from the lower left corner to the upper right corner. The closer the curve to the upper left corner, the higher the overall accuracy of the test is. Furthermore, the area under the ROC curve (AUC) is also a common measure of the clinical accuracy of a diagnostic test. The AUC from ROC analysis for $RSf_1$ is 0.948, which indicates that $RSf_1$ correlates highly with CHr. The values of AUC and ROC curve indicate that $RSf_1$ has a similar diagnostic ability as CHr in detection of absolute iron deficiency and functional iron deficiency. With a cut-off ≦102.3, $RSf_1$ had a sensitivity of 91.9% and a specificity of 82.2%, respectively.

The ROC analysis was also performed for $RSf_2$. The AUC for $RSf_2$ is 0.948. With a cut-off ≦104.73, $RSf_2$ had a sensitivity of 91.9% and a specificity of 82.2%, respectively. As shown, the ROC analysis results for both $RSf_1$ and $RSf_2$ were the same. This example shows that $RSf_1$ and $RSf_2$ are substantially equivalent in detection of iron deficiency. Herein, the cut-off refers to the cut-off values of ROC analysis of $RSf_1$ and $RSf_2$, each as defined above, with MCV and MRV expressed in femtoliter (fl). These factors are used herein as indexes for detection of iron deficiency.

Furthermore, it should be understood that the cut-off value can be different in different patient populations. For example, for renal failure patients under hemodialysis the cut-off for $RSf_1$ has been found to be about 105.1, because these patients have abnormally high MCV. While in Example 1, the patient population studied includes other conditions such as thalassemias and hemolytic anemia, the cut-off for $RSf_1$ is found to be 102.3. It is further noted that the recommended cut-off for CHr can be different depending on the specific Bayer hematology analyzer used. In a comparative study, the setting of the comparator's criterion can affect the cut-off value also. However, in a known clinical setting the cut-off value for $RSf_1$ or $RSf_2$ can be determined empirically.

It can be appreciated that when MCV is measured, what is measured is the average size or volume of the red blood cells produced in a period of 120 days before the blood sample is drawn (with the exception when the mean life time of the red blood cells is reduced). On the other hand, when MRV is measured, what is measured is the size or volume of the more recently produced red blood cells, within a period of less than 3 days before the blood sample is drawn. Since in both mature red blood cells and the reticulocytes above 90% cellular contents are hemoglobin, the sizes of these blood cells directly correlate to the hemoglobin contents of the cells. RSf, as a product function of both MCV and MRV, hence, reflects indirectly the cellular hemoglobin contents of both the reticulocytes and the mature red blood cells.

As illustrated by Example 1, RSf correlates well statistically with CHr for detection of absolute iron deficiency and functional iron deficiency. The results indicate that RSf has a similar diagnostic ability as CHr in detection of absolute iron deficiency and functional iron deficiency. It can be understood that RSf reflects the cellular characteristics under iron deficiency, or iron deficient erythropoiesis condition. In iron deficiency, two abnormal cellular features are typically observed: hypochromia (low hemoglobin content in red blood cells and reticulocytes) and microcytosis (low red blood cell and reticulocyte volumes). In the detection of iron deficiency, CHr informs the decrease of the reticulocyte hemoglobin content, i.e., hypochromic reticulocytes; while RSf informs the decreases of cellular sizes and the hemoglobin contents of both reticulocytes and red blood cells. Therefore, both RSf and CHr reflect the cellular characteristics under the iron deficiency or iron deficient erythropoiesis condition.

Furthermore, in a further embodiment, RSf can also be used, in conjunction with other biochemical indicators for determination of absolute iron deficiency and functional iron deficiency. Table 1 illustrates an example of using $RSf_1$ together with sTfR/log Ferritin. Herein, sTfR is soluble transferrin receptor. sTfR/log Ferritin, referred to as sTfR-F index, has been used clinically in diagnosis of functional iron deficiency.

TABLE 1

Diagnostic Criteria for Patients with Chronic Kidney Disease Under Hemodialysis

| | | |
|---|---|---|
| $RSf_1$ >105.1 | Actually no iron deficiency, normal hemoglobinization of red blood cells | Patients may have reduced iron supply but have not begun iron deficiency |
| $RSf_1$ <105.1 | Functional iron deficiency | Depletion of storage and functional iron compounds decreased, iron deficiency anemia (IDA) |
| | sTfR/log Ferritin: Normal | sTfR/log Ferritin: High |

In a further embodiment, the method of the present invention uses a product function of MCV and Hgb, which is herein referred to as volume-hemoglobin factor (VHf), for detection of iron deficiency, including absolute iron deficiency, latent iron deficiency and functional iron deficiency. Since microcytic anemia is a typical clinical condition resulted from iron deficiency, this factor is also referred to as microcytic anemia factor (MAf). More specifically, the method includes the following steps: (a) analyzing a blood sample of a patient on a hematology analyzer and obtaining MCV and Hgb of the blood sample; (b) obtaining VHf of the blood sample; (c) comparing the VHf to a predetermined criterion; and (d) reporting an indication of iron deficiency if the VHf meets the predetermined criterion. In a preferred embodiment, VHf is defined by the formula of (MCV×Hgb)/100.

Figure 2:
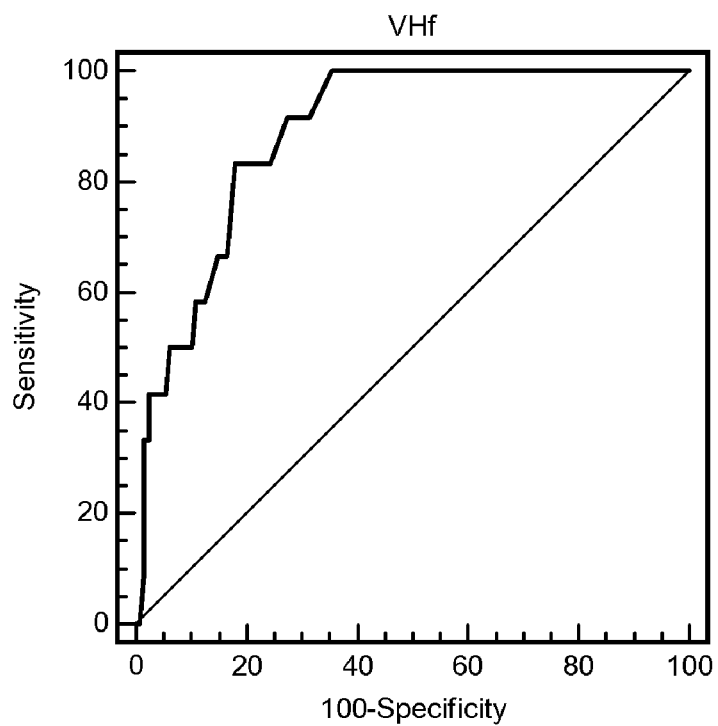
FIG. 2 is the ROC curve of VHf, using CHr as the criterion for detection of absolute iron deficiency and functional iron deficiency, as described in Example 1.

Example 1 illustrates the method of using VHf for detection of absolute iron deficiency or functional iron deficiency in comparison to CHr reported by the Bayer ADVIA 120 hematology analyzer. VHf was calculated for 1230 clinical whole blood samples using MCV and Hgb reported on the Coulter LH-750 hematology analyzer. A ROC analysis of VHf was performed using CHr <28 pg as the criterion for defining abnormal, i.e., absolute iron deficiency and functional iron deficiency. Using this criterion, 177 samples were considered abnormal and 1053 considered normal. FIG. 2 shows the obtained ROC curve of VHf. The AUC from the ROC analysis is 0.921, which indicates that VHf correlates highly with CHr. The values of AUC and ROC curve indicate that VHf has a similar diagnostic ability as CHr in detection of absolute iron deficiency and functional iron deficiency. With a cut-off ≦9.0, VHf had a sensitivity of 88.7% and a specificity of 84.8%, respectively. Herein, the cut-off refers to the cut-off value of ROC analysis of VHf as defined by the formula of (MCV×Hgb)/100, with MCV expressed in femtoliter (fl) and Hgb expressed in gram per deciliter (g/dl). This factor is used herein as an index for detection of iron deficiency. It is noted that the cut-off value can be determined in a known clinical setting, as it can vary depending on the instrument used and the patient populations.

Example 2 further illustrates the method of using VHf for detection of absolute iron deficiency and functional iron deficiency in comparison to % Hypo reported by the Bayer ADVIA 120 hematology analyzer. A ROC analysis of VHf was performed on 247 clinical whole blood samples using % Hypo >10% as the criterion for defining abnormal, i.e., absolute iron deficiency and functional iron deficiency. The AUC for VHf is 0.834. With a cut-off <10.2, VHf had a sensitivity of 81% and a specificity of 77%, respectively. The results indicate that VHf has similar diagnostic ability as % Hypo in detection of absolute iron deficiency and functional iron deficiency. Moreover, it has been found that VHf can be used for detection of absolute iron deficiency and functional iron deficiency independent of the patient's serum ferritin and TSAT levels.

Furthermore, Example 4 shows an example of using VHf for detection of latent iron deficiency in fertile, non-anemic women. As shown, the VHf value in a group of 211 fertile, non-anemic women has a statistically significant difference between the normal and the latent iron deficiency women. The results indicate that VHf can be used for detection of latent iron deficiency.

In a yet further embodiment, the present invention provides a method for detection of iron deficiency, including absolute iron deficiency, functional iron deficiency and latent functional iron deficiency, using a function of MCV, Hgb and RDW, which is herein referred to as volume-hemoglobin/distribution factor (VHDWf). The method includes the following steps: (a) analyzing a blood sample of a patient on a hematology analyzer and obtaining MCV, RDW and Hgb of the blood sample; (b) obtaining VHDWf of the blood sample using the obtained MCV, RDW and Hgb; (c) comparing the VHDWf to a predetermined criterion; and (d) reporting an indication of iron deficiency if the VHDWf meets the predetermined criterion. In a preferred embodiment, VHDWf is defined by the formula of $(MCV \times Hgb)/(RDW \times 10)$.

Figure 3A:
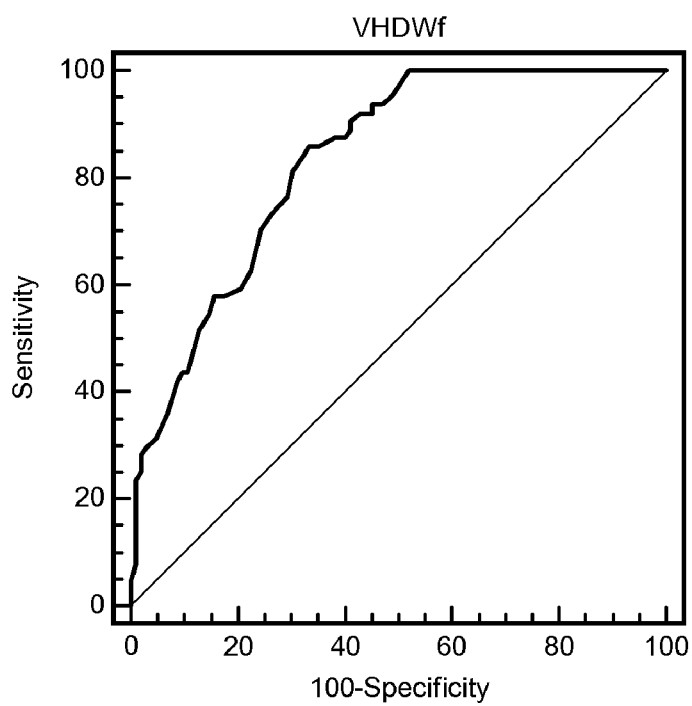
FIGS. 3A and 3B are the ROC curves of VHDWf, using % Hypo >10% and >5%, respectively, as the criteria for detection of absolute iron deficiency and functional iron deficiency as described in Example 3.

Example 3 illustrates the method of using VHDWf for detection of absolute iron deficiency and functional iron deficiency using % Hypo >10% as the criterion. A ROC analysis of VHDWf was performed on 166 clinical whole blood samples using % Hypo >10% as the criterion for defining abnormal. Using this criterion, 64 samples were considered abnormal and 102 considered as normal. FIG. 3A shows the ROC curve. The AUC from the ROC analysis was 0.832, and with a cut-off $\leq 5.0$, VHDWf had a sensitivity of 85.9% and a specificity of 66.7%, respectively. Herein, the cut-off refers to the cut-off value of the ROC analysis of VHDWf as defined by the formula of $(MCV \times Hgb)/(RDW \times 10)$, with MCV expressed in femtoliter (fl), Hgb expressed in gram per deciliter (g/dl), and RDW expressed in percentage. This factor is used herein as an index for detection of iron deficiency.

Figure 3B:
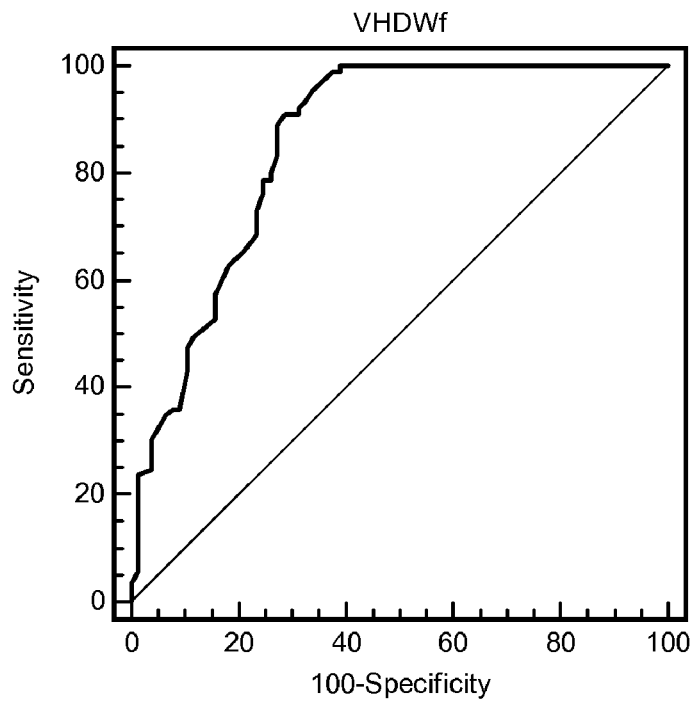

A further ROC analysis of VHDWf was performed using % Hypo >5% as the criterion for defining abnormal. Using this criterion, 89 samples were considered abnormal and 77 considered as normal. FIG. 3B shows the obtained ROC curve. The AUC was 0.857. With a cut-off $\leq 5.8$, VHDWf had a sensitivity of 91.0% and a specificity of 71.4%, respectively. These results indicate that VHDWf is highly sensitive and has a similar ability to % Hypo in detection of absolute iron deficiency and functional iron deficiency.

Figure 4:
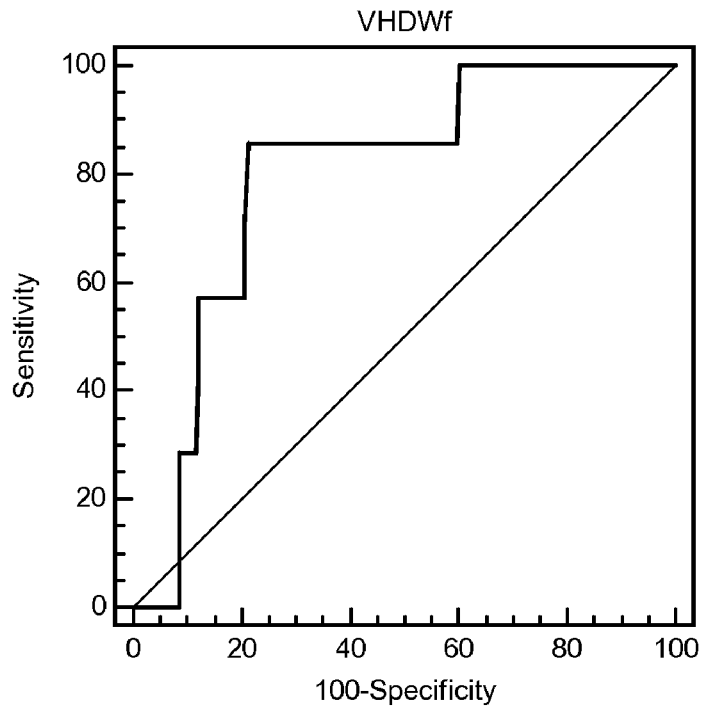
FIG. 4 is the ROC curve of VHDWf for detection of latent functional iron deficiency.

Example 4 further illustrates an example of using VHDWf for detection of latent functional iron deficiency in fertile, non-anemic women. As shown, the VHDWf value in a group of 211 fertile, non-anemic women had a statistically significant difference between the latent functional iron deficiency women and normal women. FIG. 4 shows the ROC curve of VHDWf for detection of latent functional iron deficiency. The AUC was 0.80, and with a cut-off $\leq 12.04$, VHDWf had a sensitivity of 86.7% and a specificity of 78.7%, respectively, for detection of latent functional Iron deficiency. This result indicates that VHDWf can be used for detection of latent functional iron deficiency, for this reason, it is also referred to as LFID factor (LFIDf).

Figure 5:
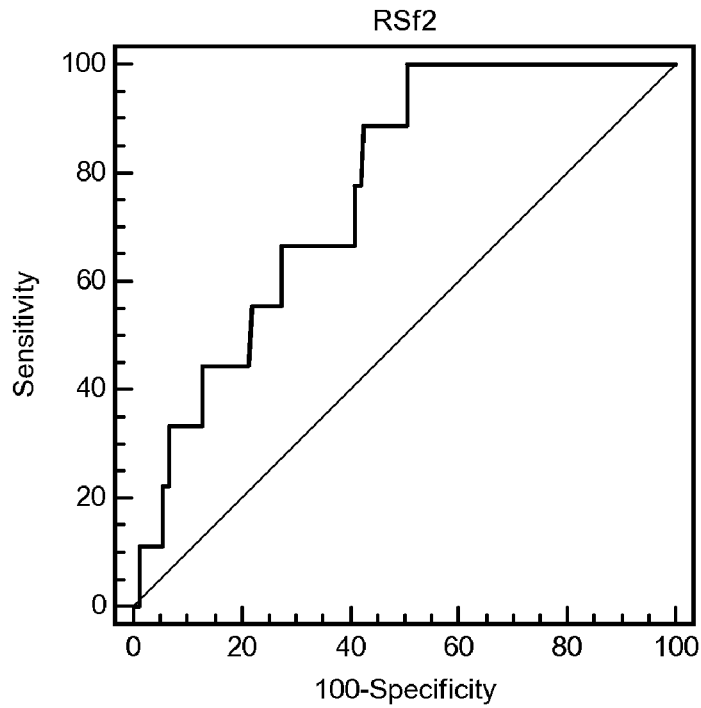
FIG. 5 is the ROC curve of RSf$_2$ for detection of hemochromatosis.

In another aspect, the present invention is further directed to a method using RSf for detection of hemochromatosis (HEM). Example 4 shows an example of using RSf for detection of hemochromatosis in fertile, non-anemic women. As shown, the $RSf_2$ value in a group of 211 fertile, non-anemic women had a statistically significant difference between the hemochromatosis women and normal women. FIG. 5 shows the ROC curve of $RSf_2$ for detection of hemochromatosis. The AUC was 0.77, and with a cut-off >92.4, $RSf_2$ had a sensitivity of 100.0% and a specificity of 49.4%, respectively, for detection of hemochromatosis. The results indicate that RSf can be used for detection of hemochromatosis.

It can be appreciated that the method of the present invention using the new parameters RSf, VHf and VHDWf in detections of iron deficiency, functional iron deficiency, latent iron deficiency, latent functional iron deficiency and hemochromatosis is a time saving and low cost approach. As described above, these parameters can be obtained from the automated reticulocyte measurement without additional cost. The turn-around time is very short, since one can obtain the hematology analysis results about 15 minutes after the blood collection from the patient.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

A cooperative study of anemia was conducted at five different participating centers in Europe, including ReCAMH, Catholic University Rome (Italy), University College Hospital, London (UK), University Clinical Centre, Ljubljana (Slovenia), Maxima Medisch Centrum, Veldhoven (Holland), Inselspital Universitätsspital, Bern (Switzerland). A total of 1230 whole blood samples were collected at these five centers and analyzed on the Coulter LH750 or Coulter GEN*S™ hematology analyzers (Beckman Coulter, Inc. Fullerton, Calif.), and on Bayer ADVIA™ 120 or 2120 hematology analyzer (Bayer Diagnostics, Tarrytown, N.Y.). The hematology analyzers were operated under their standard operating conditions, as recommended by the manufacturers. The clinical conditions included chronic kidney disease hemodialysis patients under the r-HuEPO/intravenous iron treatment, iron deficiency anemia, latent iron deficiency, and functional Iron deficiency. Iron deficiency anemia is defined by Hgb 12 g/dl and SF 22 ng/ml, and latent iron deficiency is defined by SF 22 ng/ml and Hgb >12 g/dl, if serum ferritin data were available. The absolute iron deficiency and functional iron deficiency were also identified using CHr 28 pg and/or % Hypo >10%. It is noted that in the study various normal subjects and clinical patients did not have clinical chemistry tests.

On the Coulter LH-750 or Coulter GEN*S™ hematology analyzer (Beckman Coulter, Inc., Fullerton, Calif.), the sample was analyzed using the CBC mode, and Retic mode if the reticulocyte parameters were requested by the physicians. A first aliquot of 1.6 μl of a blood sample was diluted by Isoton 3E with a dilution ratio of 6250:1, to form a first sample mixture, which was measured by the DC impedance measurements to produce the red blood cell parameters. A second aliquot of 28 μl of the blood sample was diluted with 6 ml of Isoton 3E, and then mixed with 1 ml of Lyse S III diff to form a second sample mixture. The absorption of the second sample mixture was measured at about 540 nm to obtain Hgb. A third aliquot of 34 μl of the blood sample was mixed with 0.2 ml of Retic Stain reagent, and then mixed with 2.0 ml of Retic Lyse to form the third sample mixture, which was measured by the VCS detection method to obtain the reticulocyte parameters. All reagents described above were the products of Beckman Coulter, Inc.

$RSf_1$ was calculated for 981 samples using MCV and MRV reported on the Coulter hematology analyzers, wherein both MCV and MRV were expressed in femtoliter (fl). It is noted that the blood tests were ordered by physicians, and not all samples were analyzed for reticulocyte parameters. A receiver operating characteristic (ROC) analysis was performed on $RSf_1$ using CHr <28 pg as the criterion for defining abnormal, i.e., absolute iron deficiency or functional iron deficiency. Using this criterion, 99 samples were considered abnormal and 882 considered normal. FIG. 1 shows the obtained ROC curve of $RSf_1$. The area under the ROC curve (AUC) for $RSf_1$ is 0.948. With a cut-off $\leq 102.3$, $RSf_1$ had a sensitivity of 91.9% and a specificity of 82.2%, respectively.

The ROC analysis was also performed for $RSf_2$. The AUC from the ROC analysis for $RSf_2$ was 0.948. With a cut-off $\leq 104.73$, $RSf_2$ had a sensitivity of 91.9% and a specificity of 82.2%, respectively. It is noted that the ROC analysis results for both $RSf_1$ and $RSf_2$ were the same. This example shows that $RSf_1$ and $RSf_2$ are substantially equivalent in detection of iron deficiency.

VHf was calculated for each blood sample using MCV and Hgb reported on the Coulter hematology analyzers, wherein MCV was expressed in femtoliter (fl) and Hgb was expressed in gram per deciliter (g/dl). A ROC analysis of VHf was performed using CHr <28 pg as the criterion for defining abnormal, i.e., absolute iron deficiency or functional iron deficiency. Using this criterion, 177 samples were considered abnormal and 1053 considered normal. FIG. 2 shows the obtained ROC curve of VHf. The AUC was 0.921. With a cut-off $\leq 9.0$, VHf had a sensitivity of 88.7% and a specificity of 84.8%, respectively.

EXAMPLE 2

247 whole blood samples were collected and analyzed on the Coulter LH-750 and Bayer ADVIA 120 hematology analyzers, respectively, at University College Hospital, London (UK). Both hematology analyzers were operated under their standard operating conditions.

VHf was calculated for each blood sample using MCV and Hgb reported on the Coulter LH-750 hematology analyzer, wherein MCV was expressed in femtoliter (fl), and Hgb was expressed in g/dl. A ROC analysis of VHf was performed using % Hypo >10% as the criterion for defining abnormal, i.e., absolute iron deficiency or functional iron deficiency. The AUC was 0.834. With a cut-off $\leq 10.2$, VHf had a sensitivity of 81% and a specificity of 77%, respectively.

EXAMPLE 3

166 whole blood samples were collected and analyzed on the Coulter LH750 hematology analyzer, and also analyzed on Bayer ADVIA™ 120 hematology analyzer, at University College Hospital, London (UK). The hematology analyzers were operated under their standard operating conditions. The subjects included chronic kidney disease hemodialysis patients under the treatment of r-HuEPO with i.v. iron, iron deficiency anemia, and latent Iron deficiency patients. The definitions of these conditions were the same as those described in Example 1.

VHDWf was calculated for each blood sample using MCV, Hgb and RDW reported on the Coulter LH-750 hematology analyzer, wherein MCV was expressed in femtoliter (fl), Hgb was expressed in g/dl, and RDW was expressed in percentage. A ROC analysis of VHDWf was performed using % Hypo >10% as the criterion for defining abnormal, i.e., absolute iron deficiency or functional iron deficiency. Using this criterion, 64 samples were considered abnormal and 102 considered as normal. FIG. 3A shows the ROC curve. The AUC from the ROC analysis was 0.832. With a cut-off $\leq 5.0$, VHDWf had a sensitivity of 85.9% and a specificity of 66.7%, respectively.

A further ROC analysis of VHDWf was performed using % Hypo >5% as the criterion for defining abnormal. Using this criterion, 89 samples were considered abnormal and 77 considered as normal. FIG. 3B shows the obtained ROC curve. The AUC was 0.857. With a cut-off $\leq 5.8$, VHDWf had a sensitivity of 91.0% and a specificity of 71.4%, respectively. As shown by this example, VHDWf had a high sensitivity in detection of absolute iron deficiency and functional iron deficiency.

EXAMPLE 4

Whole blood samples were collected from 211 consecutive random women with an age between 12 and 45 year old, having hemoglobin between 12 g/dl and 13 g/dl. The blood samples were analyzed on a Coulter LH750 hematology analyzer under the standard operating condition, and the complete blood count (CBC) and reticulocyte parameters were obtained. The iron profile including serum iron (Fe), transferrin (Tf), serum ferritin (SF), transferrin saturation (TSAT) was obtained on chemistry analyzers. Furthermore, for all women with SF >100 ng/ml with normal or high iron, the presence of hereditary hemochromatosis was also analyzed.

From this study, 31 latent Iron deficiency, 7 latent functional Iron deficiency, 9 hemochromatosis, and 164 with normal Iron profile were identified. Herein, latent iron deficiency is defined by SF <22 ng/ml; latent functional Iron deficiency is defined by TSAT <20% and SF >100 ng/m; and hemochromatosis is defined by SF >100 ng/ml and TSAT >50%. Furthermore, as described previously, all women involved in this study had Hgb between 12 and 13 g/dl. The genetic studies of these 9 hemochromatosis individuals showed three heterozygotic and two homozygotic mutations for the H 63 D and one heterozygotic mutation for the gen C 282 T.

$RSf_1$, $RSf_2$, VHf and VHDWf were calculated for each sample from the MCV, MRV, RDW and Hgb reported from the Coulter LH750 hematology analyzer, wherein MCV and MRV were expressed in femtoliter (fl), Hgb was expressed in g/dl, and RDW was expressed in percentage. T-student test and ROC analysis were performed on these parameters. As shown in Table 2, there was a statistically significant difference in VHf between the normal women and the latent iron deficiency women. As shown in Table 3, there was a statistically significant difference in VHDWf between the normal women and the latent functional iron deficiency women. It is noted that the cut-off values in the tables are provided from ROC analyses.

FIG. 4 shows the ROC curve of VHDWf for detection of latent functional iron deficiency. The AUC from the ROC analysis was 0.80, and with a cut-off $\leq 12.04$, VHDWf had a sensitivity of 86.7% and a specificity of 78.7%, respectively, for detection of latent functional iron deficiency.

TABLE 2

| Latent Iron Deficiency vs Normal Female | |
|---|---|
| Parameter | VHf |
| Mean of LID population | 10.8 |
| Mean of normal population | 11.2 |
| t-Student test | p = 0.0209 |
| Cut-off | $\leq 10.48$ |

TABLE 3

Latent Functional Iron Deficiency vs Normal Female

| Parameter | VHDWf |
|---|---|
| Mean of LFID population | 7.2 |
| Mean normal population | 8.0 |
| t-Student test | p = 0.0036 |
| Cut-off | ≦7.48 |

TABLE 4

Hemochromatosis vs Normal Female

| Parameter | $RSf_2$ |
|---|---|
| Mean of HEM population | 104.0 |
| Mean normal population | 93.0 |
| t-Student test | p = 0.0069 |
| Cut-off | >92.4 |

As shown in Table 4, $RSf_2$ had a statistically significant difference between the normal women and the women having hemochromatosis. A ROC analysis of $RSf_1$ was performed. FIG. 5 shows the ROC curve of $RSf_2$ for detection of hemochromatosis. The AUC was 0.77. With a cut-off >92.4, $RSf_2$ had a sensitivity of 100.0% and a specificity of 49.4%, respectively, for detection of hemochromatosis. A ROC analysis of $RSf_1$ was also performed. The AUC of $RSf_1$ was 0.77, and with a cut-off ≧96.1, $RSf_1$ had a sensitivity of 100.0% and a specificity of 49.4%, respectively. It is noted that the ROC analysis results for both $RSf_1$ and $RSf_2$ were substantially the same.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of detection of iron deficiency comprising the steps of:
    (a) analyzing a blood sample of said patient on a hematology analyzer and obtaining a mean cell volume of red blood cells (MCV) and a mean cell volume of reticulocytes (MRV) of said blood sample;
    (b) obtaining a RBC size factor (RSf) of said blood sample, defined as a product function of said MCV and said MRV;
    (c) comparing said RSf obtained in step (b) to a predetermined criterion of RSf defining iron deficiency; and
    (d) reporting an indication of iron deficiency if obtained RSf meets said predetermined criterion.

2. The method of claim 1, wherein said RSf is $RSf_1$ defined by the formula of $(MCV \times MRV)^{1/2}$.

3. The method of claim 1, wherein said RSf is $RSf_2$ defined by the formula of $(MCV \times MRV)/100$.

4. The method of claim 1, wherein said iron deficiency comprises absolute iron deficiency, or functional iron deficiency.

5. A method of detection of hemochromatosis comprising the steps of:
    (a) analyzing a blood sample of said patient on a hematology analyzer and obtaining a mean cell volume of red blood cells (MCV) and a mean cell volume of reticulocytes (MRV) of said blood sample;
    (b) obtaining a RBC size factor (RSf) of said blood sample, defined as a product function of said MCV and said MRV;
    (c) comparing said RSf obtained in step (b) to a predetermined criterion of RSf defining hemochromatosis; and
    (d) reporting an indication of hemochromatosis if obtained RSf meets said predetermined criterion.

6. The method of claim 5, wherein said RSf is $RSf_1$ defined by the formula of $(MCV \times MRV)^{1/2}$.

7. The method of claim 5, wherein said RSf is $RSf_2$ defined by the formula of $(MCV \times MRV)/100$.

8. A method of producing a RBC size factor (RSf) of a blood sample on a hematology analyzer comprising:
    (a) mixing a first aliquot of a blood sample with a blood diluent to form a first sample mixture, analyzing said first sample mixture on said hematology analyzer, and obtaining a mean corpuscular volume of red blood cells (MCV);
    (b) exposing a second aliquot of said blood sample with a reticulocyte reagent system to form a second sample mixture, analyzing said second sample mixture on said hematology analyzer, and obtaining a mean corpuscular volume of reticulocytes (MRV);
    (c) obtaining said RBC size factor (RSf) using said MCV obtained from step (a) and said MRV obtained from step (b), said RSf being defined as a product function of said MCV and said MRV; and
    (d) reporting said RSf of said blood sample on said hematology analyzer.

9. The method of claim 8, wherein said RSf is $RSf_1$ defined by the formula of $(MCV \times MRV)^{1/2}$.

10. The method of claim 8, wherein said RSf is $RSf_2$ defined by the formula of $(MCV \times MRV)/100$.

* * * * *